(12) United States Patent
Key et al.

(10) Patent No.: US 8,228,188 B2
(45) Date of Patent: Jul. 24, 2012

(54) MONITORING AND TRACKING OF WIRELESS SENSOR DEVICES

(75) Inventors: Mathew Key, Oxfordshire (GB);
Damitha Wilwara Arachchige, Oxfordshire (GB); Dougal Clarke, Oxfordshire (GB)

(73) Assignee: Toumaz Technology Limted, Oxfordshire (GB)

( * ) Notice: Subject to any disclaimer, the term of this patent is extended or adjusted under 35 U.S.C. 154(b) by 156 days.

(21) Appl. No.: 12/920,349

(22) PCT Filed: Mar. 4, 2009

(86) PCT No.: PCT/GB2009/050216
§ 371 (c)(1),
(2), (4) Date: Aug. 31, 2010

(87) PCT Pub. No.: WO2009/109779
PCT Pub. Date: Sep. 11, 2009

(65) Prior Publication Data
US 2011/0003610 A1    Jan. 6, 2011

(30) Foreign Application Priority Data
Mar. 6, 2008   (GB) .................................. 0804129.5

(51) Int. Cl.
*G08B 1/08* (2006.01)
(52) U.S. Cl. ................... 340/539.12; 600/300; 600/301; 128/903; 128/904; 340/539.24
(58) Field of Classification Search ............... 455/404.2, 455/9, 67.11, 115.1, 254; 600/300, 301; 128/903, 904; 340/539.12, 539.24, 24, 10.1; 380/270; 607/6
See application file for complete search history.

(56) References Cited

U.S. PATENT DOCUMENTS

| 5,491,837 | A | 2/1996 | Haartsen |
| 6,128,493 | A | 10/2000 | Song |
| 6,579,231 | B1 * | 6/2003 | Phipps .......................... 600/300 |
| 6,645,143 | B2 * | 11/2003 | VanTassel et al. ............. 600/300 |
| 6,665,385 | B2 * | 12/2003 | Rogers et al. ............ 379/106.02 |

(Continued)

FOREIGN PATENT DOCUMENTS
EP       1 087 630 A1    3/2001
(Continued)

OTHER PUBLICATIONS

Search Report, dated Jul. 8, 2008, issued in related GB Application No. GB 0804129.5.

(Continued)

*Primary Examiner* — Dominic E Rego
(74) *Attorney, Agent, or Firm* — Saul Ewing LLP

(57) ABSTRACT

A healthcare monitoring system includes a plurality of patient wearable sensor devices for the purpose of monitoring physiological data, each sensor device including a radio frequency transceiver. A plurality of base stations are provided at respective fixed locations within a healthcare facility, each base station including a radio frequency transceiver for communicating with one or more of the sensor devices for the purpose of receiving monitored physiological data. A central server is coupled to the base stations for the purpose of receiving and recording monitored physiological data. Each sensor device is arranged in use to attach to a first base station that is within range, and to attach to a second, different base station that is within range when contact with the first base station is lost, attachment of the sensor device to a base station being registered with the central server.

15 Claims, 2 Drawing Sheets

U.S. PATENT DOCUMENTS

| | | | |
|---|---|---|---|
| 6,738,671 B2* | 5/2004 | Christophersom et al. | 607/60 |
| 6,847,294 B1* | 1/2005 | Lin et al. | 340/539.12 |
| 6,897,788 B2* | 5/2005 | Khair et al. | 340/870.16 |
| 6,940,403 B2* | 9/2005 | Kail, IV | 340/539.12 |
| 7,247,136 B2* | 7/2007 | Feliss et al. | 600/300 |
| 7,400,257 B2* | 7/2008 | Rivas | 340/573.1 |
| 7,595,723 B2* | 9/2009 | Heitzmann et al. | 340/539.12 |
| 7,924,150 B2* | 4/2011 | Baldus et al. | 340/539.12 |
| 7,955,258 B2* | 6/2011 | Goscha et al. | 600/300 |
| 7,978,063 B2* | 7/2011 | Baldus et al. | 340/539.12 |
| 8,081,071 B1* | 12/2011 | Vaisnys et al. | 340/539.12 |
| 2002/0013517 A1 | 1/2002 | West et al. | |
| 2002/0103514 A1* | 8/2002 | Abrahamson | 607/60 |
| 2003/0182158 A1* | 9/2003 | Son | 705/2 |
| 2004/0147818 A1 | 7/2004 | Levy et al. | |
| 2005/0009542 A1 | 1/2005 | Oprescu-Surcobe et al. | |
| 2006/0279643 A1* | 12/2006 | Levien et al. | 348/231.3 |
| 2007/0152811 A1 | 7/2007 | Anderson | |
| 2008/0004904 A1 | 1/2008 | Tran | |

FOREIGN PATENT DOCUMENTS

| | | |
|---|---|---|
| WO | WO 02/35997 A1 | 5/2002 |
| WO | 2008/029362 A2 | 3/2008 |
| WO | WO 2009/032134 A2 | 3/2009 |

OTHER PUBLICATIONS

International Search Report, dated Jun. 26, 2009, issued in priority International Application No. PCT/GB2009/050216.

International Preliminary Report on Patentability (IPRP), dated Jul. 8, 2010, issued in priority International Application No. PCT/GB2009/050216.

McKean and Gough, IEEE Transactions on Biomedical Engineering, vol. 35, No. 7, pp. 526-532 (1988).

Daniloff, George Y., Diabetes Technology & Therapeutics, vol. 1, No. 3, pp. 261-266 (1999).

Atanasov et al., Med. Eng. Phys., vol. 18, No. 8, pp. 632-640 (1996).

* cited by examiner

MONITORING AND TRACKING OF WIRELESS SENSOR DEVICES

CROSS REFERENCE TO RELATED APPLICATIONS

This application claims the priority of PCT/GB2009/050216, filed on Mar. 4, 2009, which claims priority to Great Britain Application No. 0804129.5, filed Mar. 6, 2008, the entire contents of which are hereby incorporated in total by reference.

FIELD OF THE INVENTION

The present invention relates to a method and apparatus for monitoring and tracking wireless sensor devices and is applicable in particular, though not necessarily, to the monitoring and tracking of such devices in a hospital or other location where healthcare services are provided.

BACKGROUND TO THE INVENTION

A "biosensor" has been defined as an analytical device incorporating a biological or biologically-derived sensing element either integrated within or intimately associated with a physicochemical transducer. Biosensors are generally designed to produce either discrete or continuous digital electronic signals that are proportional to a single analyte or a related group of analytes, although the provision of analogue signals should not be excluded.

There are many areas of application for biosensors including for example environmental sensing, chemical production, and food and drink production and preparation. One area of application that has attracted a great deal of interest however is that of medical diagnostics, monitoring, and treatment. The following discussion addresses primarily these medical applications, although it will be appreciated that the problems and solutions considered may also have non-medical applications.

Biosensors that are either implantable or wearable on a patient's skin can provide substantially continuous monitoring of a given condition and offer the prospect of closed loop treatment systems, where treatment is applied in direct response to the monitored values, as well as giving feedback to users and clinicians. For example, proposals have been made and systems produced that inject insulin into a patient's system in response to the detection of a low blood sugar level. Both types of sensor, implantable and wearable, are likely to have their own distinct advantages, and will be used in different circumstances and to monitor and treat different conditions.

A number of factors are likely to be key to the successful development of commercially viable implantable and wearable biosensors. Chief amongst these is the need for low power consumption. Particularly in the case of implantable sensors, battery life must be extremely long, as surgical intervention would be required to replace a battery. In addition to minimising device power consumption levels, consideration has been given to powering devices using the electrochemical reaction of bodily substances, and even using electric and magnetic fields generated by the body (so-called energy scavenging techniques). In the case of wearable sensors that are likely to be disposable, low cost is also a priority.

To provide substantially continuous monitoring of data from implantable and/or wearable sensors it is necessary to transmit data between the sensor and some monitoring and control system using some form of wireless transmission mechanism. As it is important to minimise the power consumption of such sensors, wireless transmission (e.g. via RF signals) must be at low power and therefore of limited range, and as such requires that the corresponding receiving equipment must be situated within close proximity to the transmitting sensor device. This can be achieved by the patient wearing or carrying a transceiver device, for example, in the form of a wireless PDA or smart phone, which can process and display the data received from the sensors and can retransmit this data, at higher powers, over a suitable access network to, for example, a central monitoring and processing computer system. Alternatively, this could be achieved through a network of numerous transceiver devices (or "base stations") distributed throughout a location where monitoring is of specific importance, such as a hospital, a care home or other facility, and with which the sensors communicate directly. The provision of such a network for receiving the sensor data transmissions removes the need for each individual to carry a transceiver device and provides a means for tracking the location of each sensor within the network.

In order to successfully implement substantially continuous monitoring and tracking of sensors using a network of transceivers or "base stations", any system must incorporate a method of allowing each sensor to connect with a base station within close proximity and also allow each sensor to move throughout the network and be handed-off from one base station to another.

U.S. Pat. No. 6,441,747 describes a wireless programmable system for medical monitoring that includes a base unit designed to communicate with a plurality of worn biosensor transceivers. Other documents relevant to this field are: IEEE Trans Biomed Eng, vol 35, no 7, July 1988, p 526-532; Diabetes Technol Ther, vol 1, no 3, 1999, p 261-6; Med Eng Phys, vol 18, no 8, 1996 December , p 632-40; US20010041831; and WO2000067633.

SUMMARY OF THE INVENTION

According to a first aspect of the present invention there is provided a healthcare monitoring system comprising a plurality of sensor devices for attachment to patients for the purpose of monitoring physiological data, each sensor device comprising a radio frequency transceiver. The system further comprises a plurality of base stations arranged in use to be placed at respective fixed locations within a healthcare facility, each base station comprising a radio frequency transceiver for communicating with one or more of said sensor devices for the purpose of receiving monitored physiological data. A central server is coupled to said plurality of base stations for the purpose of receiving and recording monitored physiological data. Each sensor device is arranged in use to attach to a first base station that is within range, and to attach to a second, different base station that is within range when contact with said first base station is lost, attachment of the sensor device to a base station being registered with said central server. Each said base station is configured at initialisation, or upon detection of interference on a used channel, to perform a channel selection process, the process comprising retrieving from said central server a list of currently unallocated channels within the system and scanning said unallocated channels to determine if one channel is available. If a channel is available, the base station selects that channel and notifies the central server of the selection. If none of the unallocated channels is available, the base station retrieves from said central server a list of currently allocated channels within the system, and scans said channels to determine if one channel is available and, if so, selecting that channel and notifying the central server of the selection.

Embodiments of the invention provide a complete healthcare monitoring solution which utilises a lightweight radio interface able to handle the roaming of patients within a facility.

Preferably, each said sensor device is configured to identify a base station to which to attach by scanning a predefined set of frequency channels to identify a channel on which an Invite is being broadcast with sufficient strength. Said central server is configured to maintain said allocated and unallocated channel lists and to update said lists when notified of a selection by a base station.

Preferably the system comprises a local area network to which said central server is connected, and a plurality of relay stations coupling said base stations to the local area network. Each said relay station couples a plurality of base stations to the local area network.

Preferably, each said sensor device is configured at power-up to transmit its identity to said central server via the base station to which it is attached. Said central server is configured to receive said identity and to record the current location of the sensor device, to determine a default configuration for said sensor device based upon the location of the device, and to transmit that default configuration to the sensor device, the sensor device being configured to receive and install the default configuration.

Preferably, each said base station is configured to allocate to each attached sensor device, communication slots during which duplex communication between the base station and the sensor device can occur. Each said sensor device is configured to turn its radio interface on at the beginning of an allocated slot and to turn its radio interface off before the end of an allocated slot. Further, each said base station is configured to periodically allocate a ping slot to each sensor device, in the absence of any other data exchange, to transmit a ping request to each sensor device in the allocated ping slot in order to determine the presence status of each device.

Each sensor device may also be configured to determine that contact with the first base station has been lost when it has not received a given number of ping requests. Preferably, each sensor device is configured to buffer monitored physiological data during a time period when contact with the first base station has been lost and before attachment to a second base station, and to then send this buffered data to the second base station when attached to the second base station.

Preferably, one or more monitoring stations ("nurse stations") is/are coupled to said central server and to said base stations, the monitoring stations being configured to allow the monitoring of data recorded by the sensor devices and the programming of the sensor devices.

The system may comprise a wireless barcode scanner configured to scan barcodes present on the sensor devices, and to transmit this data to said central server together with identities of patients using the sensor devices.

According to a second aspect of the present invention there is provided a sensor device suitable for attaching to the body of a patient and comprising a radio frequency transceiver suitable for communicating with a radio base station, the device being configured at power-up to transmit its identity to a central server and to receive and install a default operating configuration sent in response by the central server.

According to a third aspect of the present invention there is provided a sensor device suitable for attaching to the body of a patient and comprising a radio frequency transceiver suitable for communicating with a radio base station, the device being configured to synchronise a local clock with a clock of a base station to which the device is attached, and to power-up its radio frequency transceiver only for time slots identified to it by the base station.

The sensor device may be configured to receive in a slot, an indication of the next slot start time, and to power up the radio frequency transceiver at that next slot start time.

DETAILED DESCRIPTION OF CERTAIN EMBODIMENTS OF THE INVENTION

Figure 1:
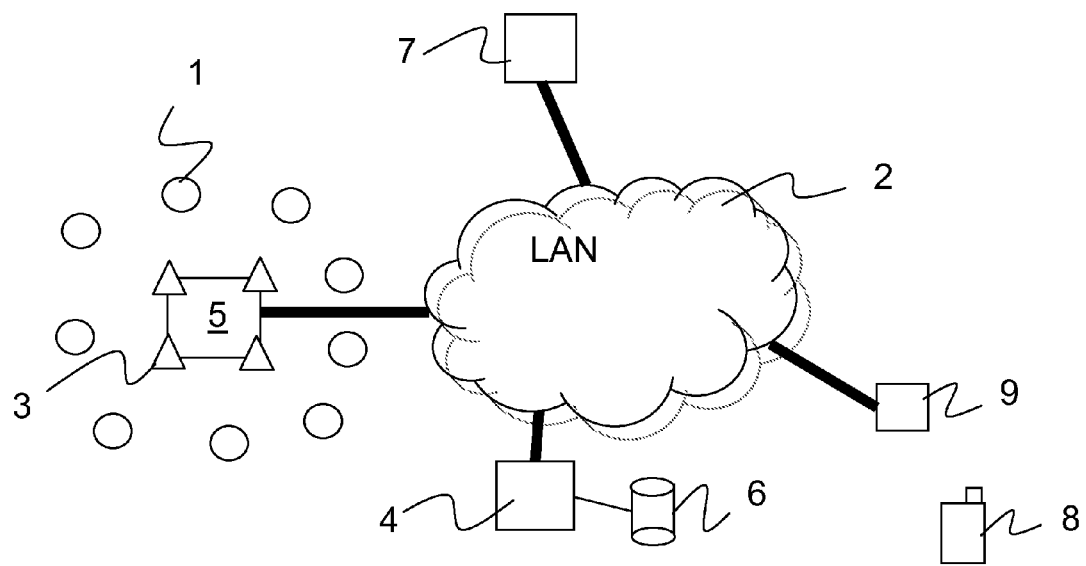
FIG. 1 illustrates schematically a network architecture for monitoring and tracking of low power wireless sensor devices.
Figure 2:
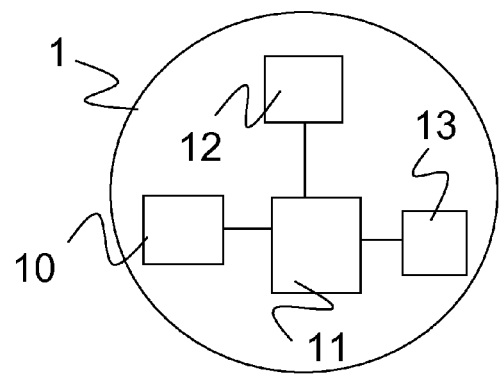
FIG. 2 illustrates schematically a patch-like sensor device for use with the network of FIG. 1.

FIG. 1 illustrates schematically an example network architecture which could be implemented in a hospital or other healthcare location within which the monitoring and tracking of low power wireless sensor devices is required. The network comprises a number of wireless sensor devices 1, one of which is illustrated further in FIG. 2. In this example, the sensor devices are patch-like devices ("patches") into each of which is integrated one or more sensors (which may be biosensors, electrodes for monitoring ECG/EEG signals, etc) 10, analogue/digital processing circuitry 11, memory 12, and an RF transceiver 13. In use, the patches 1 are worn on the bodies of patients. The network further comprises a wired (or possibly wireless) Local Area Network (LAN) 2 to which are attached a number of components which will now be described.

A plurality of base stations 3 act as wireless access points to the LAN, with each base station having an RF transceiver for communicating with in-range patches 1. Base stations are grouped according to location, with each group of base stations (typically four) being coupled to a relay station 5. Base stations are coupled to respective ports on a given relay station, with the relay station providing a TCP/IP interface to the LAN.

The relay stations are in turn coupled (in a logical sense) to a central patch server 4. The central patch server 4 maintains, within a patch database 6, information relating to all currently active patches 1, including for each patch: a patch identity (e.g. a unique tag programmed into a memory of each patch), a patient identity for the patient currently using the patch, the frequency channel on which the patch is communicating, and the patch location as defined by the base station and relay station with which the patch is currently associated. In addition, the patch server 4 maintains information pertaining to the movement of the patient within the hospital as defined by the base stations to which the patch has been attached and the times at which base station hand-offs occurred.

Other record and monitoring systems may be connected directly to the LAN, or may be coupled thereto, e.g. via an Internet connection of Wide Area Network (WAN) link. For example, one such system may be a hospital patient records system which maintains patient healthcare records.

Returning to the schematic of FIG. 1, a plurality of nurse stations are also coupled to the LAN 2. Each nurse station provides an interface to the central patch server 4 that allows nurses and other healthcare staff to view data recorded from any currently (or previously) active patch 1, including in particular sensed data and location. Additionally, the nurse stations can be programmed with alarms to provide warnings to healthcare staff, e.g. on the basis of sensed data received from a patch, when a patient roams from or to a particular area, or when a patch is no longer communicating with the network. A nurse station 7 may comprise a personal computer running an appropriate software application.

For the purpose of wireless communication between the patches and the base stations, the system makes use of an allocated part of the RF spectrum which is divided up to provide a number of discrete channels. Individual base stations 3 are each allocated one channel from this set of available channels under the control of the central patch server 4 which maintains a record of currently allocated and unallocated channels. The patch server allocates channels in cooperation with base stations in such a way as to avoid or at least minimise interference between neighbouring base stations (and possibly other RF equipment).

It will be appreciated that in the healthcare arena, system reliability is of critical importance. In particular, the system must be robust against interference, whilst at the same time having the flexibility to re-organise components of the communication network(s), and to expand (and contract) the system. Key to this is a mechanism for dynamically allocating radio channels to the base stations 3 from the available set of channels.

Figure 3:
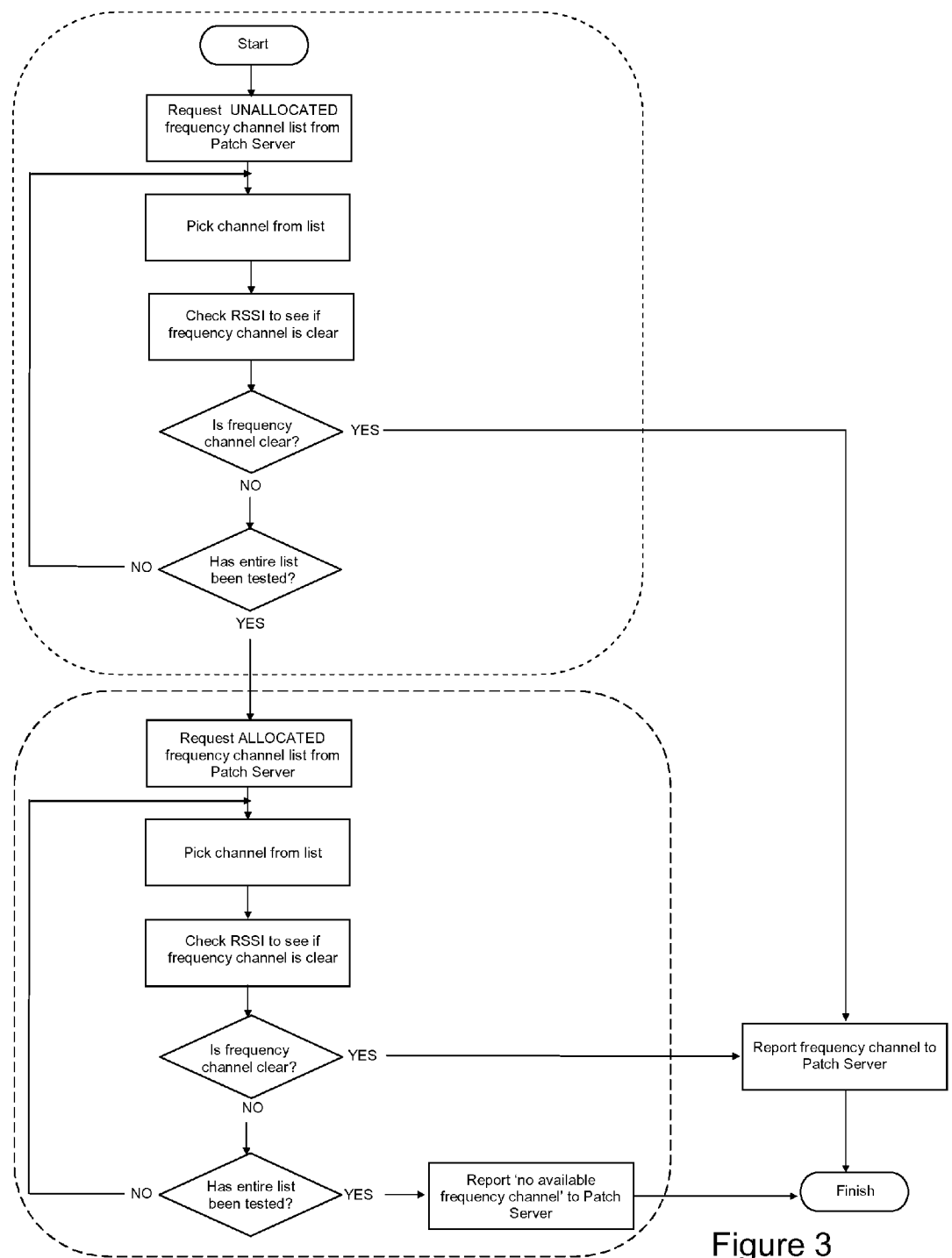
FIG. 3 is a flow diagram illustrating a method of allocating a frequency channel to a base-station.

FIG. 3 is a flow diagram illustrating a procedure by which a base station 3 is allocated a radio channel by the central patch server 4. When a base station is initialised, or when the channel in use by a base station becomes blocked, the base station 3 requests from the central patch server 4 a list of the currently unallocated channels (from the available set), i.e. a list of the channels not currently being used by any other base station within the system. It is assumed here that, as the location covered by the system is likely to be relatively small, reuse of channels anywhere within the location should be avoided (at least in the first instance). Of course, for larger coverage areas, the patch server 4 may implement a more sophisticated channel allocation algorithm, whereby channel reuse is permitted providing that base stations are sufficiently far apart.

Upon receiving a list of unallocated channels from the central patch server 4, a base station 3 measures the received signal strength on each unallocated RF channel in turn (the measure being termed the "received signal strength indicator" or RSSI). If the RSSI for a channel indicates that the channel is free from interference, the base station selects that frequency for use, and sends a notification to the patch server. The patch server records that channel as allocated and updates its channel/base station allocation list. However, if the measured RSSI indicates that a channel is not useable, the base station turns to the next unallocated channel, and repeats the RSSI measurement for that channel.

If none of the channels (identified by the central patch server as unallocated) are available to the base station, the base station informs the patch server and requests a list of currently allocated channels, i.e. including those channels identified by the patch server as being in use by another base station. The base station then repeats the RSSI measurement for each of the allocated channels in turn to determine if any of these are available. If a particular channel is currently allocated to a relatively distant base station, and there is no local interference, then the searching base station may well determine that the channel is available to it. If so, the base station notifies the patch server which updates its allocated channel list (to indicate that the channel has been allocated to a further base station). If the base station still cannot identify an available channel then it reports this to the central patch server. The patch server may reissue an updated list of unallocated channels to the base station, which can then repeat the process. This can continue until an available channel is identified by the base station, or until some predefined time period has elapsed, whereupon system maintenance action (alarm) is triggered.

Assuming that a base station 3 has identified an available channel, it begins broadcasting an "Invite" message on this channel at regular intervals. An Invite is broadcast as long as the base station has a slot available for a patch. Once all of its slots have been allocated (eight in this example), the broadcasting of Invites is turned off until a slot becomes available again.

A base station coordinates communications with attached patches by allocating slots to those patches. Within a given slot, duplex communication occurs between the base station 3 and a given patch 1. Each patch turns on its radio interface at the beginning of an allocated slot and turns it off before the end of each slot. During an allocated slot, the base station instructs the patch when it should next wake up, and how long it has to transfer its new sensor readings. Clock synchronisation (between the patch and base station clocks) occurs during a slot. Slot size is dynamic and is set according to demand and capacity and to ensure that only a single patch is communicating with a given base station at any given time. However, a base station must send a "ping" message to each attached patch with a regular frequency (e.g. every 16 seconds) and a patch is configured to wake up for at least a short period to receive and respond to the ping. This ping procedure is used to determine whether a patch is still connected to the base station or whether it has roamed away or otherwise lost connectivity. If there is no response to a ping for a given number of attempts, then the base station notifies the server that the patch has roamed away.

When a patch 1 is first activated, e.g. by enabling a power source of the patch, the patch powers-up its radio interface, and begins cycling through a predefined channel list, listening on each for a broadcast Invite. When the patch detects an Invite (an RSSI test may be used to if multiple Invites from different base stations are received) it responds with a "Hello" message. Each Invite identifies the slot within which the patch can respond. This slot may be a current slot, in which case the patch responds immediately with the Hello message, or it may be some later slot in which case the patch may power-down the radio interface and wake it up at the commencement of that later slot. In either case, the patch includes within the Hello a unique patch identifier. The base station 3 receives the hello response, and forwards this to the central patch server 4 via the attached relay station 5. Once a patch 1 has attached to a base station 3 it can transmit data to that base station during its allocated slot. This data can either be unprocessed data collected by the patch, or data that has also undergone some processing at the patch. In the periods between its allocated transmission slots, the patch 1 buffers the data collected during that period in its memory until it can transmit this data during its next allocated slot.

The central patch server 4 maintains a record of issued patch identifiers (IDs) and is able to determine the version number of software preinstalled on the patch 1. If necessary, the patch server 4 is able to install a software upgrade into the patch 1 via the relay station 5 and base station 3. The patch server also determines the location of the patch and retrieves a default configuration for this location. The default configuration is installed into the patch 1. By way of example, a default configuration for a patch located with an emergency hospital ward may require more frequent sensor measurements that for that for a patch located within a general hospital ward. The default configuration is also stored by the base station 3. The base station uses the configurations for all attached patches to perform slot allocation.

Assuming that the patch is now attached to a patient, a handheld scanner 8 with wireless link (e.g. via wireless access point 9) to the LAN 2 is used to scan a barcode printed on the patch. This barcode contains the unique patch ID. A nurse or other operator then enters the patient's name (by manual entry or database lookup) into the scanner 8, and the data is sent to the central patch server 4. The patch server logs the patient's name against the patch ID and default configuration. A nurse is then able to log-on to the system at a nurse station 7 and view the default configuration for the patient. Appropriate, patient specific, changes may be made to the configuration by entering data into the nurse station 7 and sending this to the patch via the relay station 5 and base station 3 (the base station also records changes and alters the slot allocation accordingly). Recorded data, stored at the central patch server 4, can also be accessed via the nurses' station 7. Via the nurse station 7, a nurse may also request an on-demand measurement from the patch, e.g. return a 10 second ECG measurement.

If a patch 1 does not receive a ping request from the base station to which it is currently attached within a given period of time (e.g. equivalent to a given number of ping requests that it would expect to receive) then the patch will interpret this to mean that it has lost communication with that base station. For example, this may occur if the wearer of a patch has roamed out of the coverage area of that base station, or the channel currently being used by that base station has become unusable.

When a patch determines that it has lost communication with a base station it will again cycle through the predefined channel list, listening on each for a broadcast Invite, in order to establish a new attachment to a base station. This process could result in the patch re-attaching to the same base station on the same channel, if the channel has again become usable, or to the same base station on an alternative channel selected by the base station in cooperation with the central patch server 4, or to a different base station.

During the period when a patch does not have an attachment to a base station, the patch will buffer the data collected during that period in its memory, until a new attachment has been established and it can transmit this data to the network.

If the wearer of a patch 1 that is attached to a base station 3 roams out of the coverage area of that base station, or the channel currently being used by the patch becomes unusable (e.g. due to interference), then the base station will detect the "loss" of the patch (e.g. due to a failure on the part of a patch to respond to the ping request) and will report this to the central patch server which can issue an alert, e.g. to the nurse station, if appropriate. Assuming that the patch attaches to a new base station, this base station will update the central patch server with the patch's new location which can cancel any alert. As has already been mentioned, if the communication failure is due to continued interference, the base station will detect this, inform the patch server, and repeat the channel selection procedure of FIG. 3.

It is noted that when a radio link goes down, the patches previously using that link should not all simultaneously switch to the same channel and respond to the first base station to broadcast an "Invite" message. This is avoided by allowing the patches to select a new channel at random, and to start the channel search from that randomly selected channel.

It will be appreciated by those of skill in the art that various modifications may be made to the above described embodiments without departing from the scope of the present invention. For example, a base station may be configured to accept an "alarm" signal from any patch during its "listening" periods. This will allow, for example, a cardiac arrest alert to be relayed immediately to the central patch server and the nurses' station(s) without the associated patch having to wait for its next allocated wake-up slot.

The invention claimed is:

1. A healthcare monitoring system comprising:
a plurality of sensor devices for attachment to patients for the purpose of monitoring physiological data, each sensor device comprising a radio frequency transceiver;
a plurality of base stations arranged in use to be placed at respective fixed locations within a healthcare facility, each base station comprising a radio frequency transceiver for communicating with one or more of said sensor devices for the purpose of receiving monitored physiological data; and
a central server coupled to said plurality of base stations for the purpose of receiving and recording monitored physiological data,
wherein each sensor device is arranged in use to attach to a first base station that is within range, and to attach to a second, different base station that is within range when contact with said first base station is lost, attachment of the sensor device to a base station being registered with said central server; and
each said base station being configured at initialisation, or upon detection of interference on a used channel, to perform a channel selection process, the process comprising:
retrieving from said central server a list of currently unallocated channels within the system;
scanning said unallocated channels to determine if one channel is available and, if so, selecting that channel and notifying the central server of the selection;
if none of the unallocated channels is available, retrieving from said central server a list of currently allocated channels within the system; and
scanning said allocated channels to determine if one channel is available and, if so, selecting that channel and notifying the central server of the selection.

2. A system according to claim 1, each said sensor device being configured to identify a base station to which to attach by scanning a predefined set of frequency channels to identify a channel on which an Invite is being broadcast with sufficient strength.

3. A system according to claim 1, said central server being configured to maintain said allocated and unallocated channel lists and to update said lists when notified of a selection by a base station.

4. A system according to claim 1 and comprising a local area network to which said central server is connected, and a plurality of relay stations coupling said base stations to the local area network.

5. A system according to claim 4, wherein each said relay station couples a plurality of base stations to the local area network.

6. A system according to claim 1, wherein each said sensor device is configured at power-up to transmit its identity to said central server via the base station to which it is attached.

7. A system according to claim 6, wherein said central server is configured to receive said identity and to record the current location of the sensor device.

8. A system according to claim 7, wherein said central server is configured to determine a default configuration for said sensor device based upon the location of the device, and to transmit that default configuration to the sensor device, the sensor device being configured to receive and install the default configuration.

9. A system according to claim 1, each said base station being configured to allocate to each attached sensor device communication slots during which duplex communication between the base station and the sensor device can occur.

10. A system according to claim 9, each said sensor device being configured to turn its radio interface on at the beginning of an allocated slot and to turn its radio interface off before the end of an allocated slot.

11. A system according to claim 9, each said base station being configured to periodically allocate a ping slot to each sensor device and, in the absence of any other data exchange, to transmit a ping request to each sensor device in the allocated ping slot in order to determine the presence status of each device.

12. A system according to claim 11, each sensor device being configured to determine that contact with the first base station has been lost when it has not received a given number of ping requests.

13. A system according to claim 1, each sensor device being configured to buffer monitored physiological data during a time period when contact with the first base station has been lost and before attachment to a second base station, and to then send this buffered data to the second base station when attached to the second base station.

14. A system according to claim 1 and comprising one or more monitoring stations coupled to said central server and to said base stations, the monitoring stations being configured to allow the monitoring of data recorded by the sensor devices and the programming of the sensor devices.

15. A system according to claim 1 and comprising a wireless barcode scanner configured to scan barcodes present on the sensor devices, and to transmit this data to said central server together with identities of patients using the sensor devices.

* * * * *